United States Patent
Smith, Jr. et al.

(10) Patent No.: US 11,230,508 B1
(45) Date of Patent: Jan. 25, 2022

(54) GREEN OXIDIZER COMPOSITIONS AND METHODS

(71) Applicants: James Edwin Smith, Jr., Gulf Breeze, FL (US); Chen Zhang, San Jose, CA (US); Yu Lei, Huntsville, AL (US)

(72) Inventors: James Edwin Smith, Jr., Gulf Breeze, FL (US); Chen Zhang, San Jose, CA (US); Yu Lei, Huntsville, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 692 days.

(21) Appl. No.: 16/042,746

(22) Filed: Jul. 23, 2018

Related U.S. Application Data

(60) Provisional application No. 62/535,630, filed on Jul. 21, 2017.

(51) Int. Cl.
| | |
|---|---|
| *D03D 23/00* | (2006.01) |
| *D03D 43/00* | (2006.01) |
| *C06B 25/34* | (2006.01) |
| *C07D 305/08* | (2006.01) |
| *C06B 47/08* | (2006.01) |
| *C06B 25/00* | (2006.01) |

(52) U.S. Cl.
CPC ............ *C06B 25/34* (2013.01); *C07D 305/08* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,557,181 | A * | 1/1971 | Lakritz et al. | C08G 65/22 568/589 |
| 5,837,930 | A * | 11/1998 | Mul | C06B 47/10 149/19.6 |
| 9,481,840 | B2 | 11/2016 | Smith et al. | |
| 10,858,296 | B1 * | 12/2020 | Myrick | C06B 33/00 |
| 2010/0287824 | A1 | 4/2010 | Smith, Jr. et al. | |
| 2014/0090756 | A1 * | 4/2014 | Reid | B22F 1/0062 149/11 |
| 2014/0194645 | A1 * | 7/2014 | Anderson | B29B 17/0206 560/129 |
| 2014/0227548 | A1 * | 8/2014 | Myrick | C10L 1/28 428/570 |

(Continued)

OTHER PUBLICATIONS

Hampton, et al., "Atmospheric Effects on the Chemical Delay Time for Hypergolic Biopropellants," AIAA paper 2004-1381, AIAA 42nd Aerospace Sciences Meeting and Exhibit, Jan. 2004.

(Continued)

*Primary Examiner* — James E McDonough
(74) *Attorney, Agent, or Firm* — Jon E. Holland; Maynard, Cooper & Gale, P. C.

(57) ABSTRACT

The present disclosure generally pertains to green oxidizer compositions and method of synthesizing and using the same. Such green oxidizers are stable, may be used in conventional bipropellant thrusters, including, but not limited to LDACS applications, and offer several benefits over conventional oxidizers with respect to toxicity and/or corrosion. The present disclosure also relates to methods of synthesizing poly-nitrated oxetane, a green oxidizer, in an Argon-rich environment.

6 Claims, 18 Drawing Sheets

(56) References Cited

U.S. PATENT DOCUMENTS

2015/0141540 A1* 5/2015 Golding .................... C06C 9/00
521/168

OTHER PUBLICATIONS

Hampton, et al., "Importance of Chemical Delay Time in Understanding Hypergolic Behaviors," AIAA paper 2003-1359, AIAA 41st Aerospace Sciences Meeting and Exhibit, Jan. 2003.
Carolan, et al., Simple 3-Substituted Oxetanes, Doctor of Philosophy Thesis, University of Salford, Apr. 1992, 148 pages.
Huzel, et al., "Design of Liquid Propellant Rocket Engines," National Aeroautics and Space Administration, 1967.
Krzycki, "How to Design, Build, and Test Small Liquid-Fuel Rocket Engines," Rocketlab, 1967, pp. 1-71.
Searles, et al., "Comprehenzive Heterocyclic Chemistry," Pergamon, 1984, vol. 7, p. 363.

* cited by examiner

GREEN OXIDIZER COMPOSITIONS AND METHODS

CROSS-REFERENCE TO RELATED APPLICATION

This application claims priority to U.S. Provisional Patent Application No. 62/535,630, entitled "Green Oxidizer Development" and filed on Jul. 21, 2017, which is incorporated herein by reference.

STATEMENT REGARDING FEDERALLY SPONSORED RESEARCH OR DEVELOPMENT

This invention was made with government support under Grant Number HQ0147-13-C-6028 awarded by the Missile Defense Agency. The government has certain rights in the invention.

BACKGROUND OF THE INVENTION

Hypergolic compounds—a fuel and an oxidizer capable of ignition upon combination—are used in a wide range of propellant applications due to the lack of need for a separate ignition source and their relative simplicity. Combinations typically include hydrazine-based fuels and oxidizers such as nitrogen tetroxide or inhibited red fuming nitric acids. Unfortunately, these propellants are often highly toxic and carcinogenic to humans, rendering their use expensive and potentially unsafe. Given these concerns, there is much interest in alternative fuels and oxidizers that do not pose such risks.

There has been a great deal of recent research on the development of green fuels. With respect to the development of green oxidizers, however, efforts have been limited. Of those limited efforts, most work on green oxidizers has focused on peroxide, which is notoriously unstable. Other oxidizers, such as $N_2O_4$, MON, $MON_3$, and their variants are toxic and/or corrosive, rendering them unsuitable or undesirable for use. As such, there remains an unmet need to develop and optimize green oxidizer formulations that are hypergolic with traditional hydrazines and which may be extended to use with ionic liquid fuels (HGF) for Liquid Propulsion Divert and Attitude Control System (LDACS) applications.

SUMMARY OF THE INVENTION

In one embodiment, the present disclosure relates to a method of synthesizing poly-nitrated oxetane comprising the steps of: flushing an empty reactor with Argon so that the entire synthesis process occurs within an Argon environment; adding fuming nitric acid to sulfuric acid (the nitrating mixture); cooling the nitrating mixture to 0° C.; mixing the nitrating mixture with a stir bar; slowly adding a 3-hydroxyoxetane mixture to the nitrating mixture to form a reaction mixture; stopping the stirrer while adding 3-hydroxyoxetane and resuming mixing the reaction mixture in between the additions; stirring the reaction mixture at room temperature for one additional hour at room temperature; and quenching the reaction mixture with deionized water with ice. In certain embodiments, the method further comprises the step, after quenching, of allowing the resulting poly-nitrated oxetane to settle to the bottom of the reactor and separate from the aqueous layer. In certain embodiments, the method further comprises the step, after quenching, of collection of the poly-nitrated oxetane. In yet another embodiment, the method further comprises the step of reducing the moisture content in the collected poly-nitrated oxetane by vacuum evaporation. In certain embodiments, the vacuum evaporation is performed using a water temperature of 38° C. for 5-8 hours. In certain embodiments, the poly-nitrated oxetane is collected by freezing the poly-nitrated oxtene such that the poly-nitrated oxetane separates from a layer allowing the top layer to be decanted.

In another embodiment, the present disclosure relates to a bipropellant composition for use in thrusters comprising: poly-nitrated oxetane; and a fuel. In certain embodiments, the fuel is an ionic liquid fuel. In certain embodiments, the fuel is HGF-A. In certain embodiments, the fuel is HGF-B. In certain embodiments, the fuel is hydrazine. In certain embodiments, the composition is configured for use in Liquid Propulsion Divert and Attitude Control Systems.

In another embodiment, the present disclosure relates to a method of propulsion comprising spraying poly-nitrated oxetane and a fuel within a combustion chamber of a thruster. In certain embodiments, the combustion chamber is heated prior to spraying the poly-nitrated oxetane and fuel. In certain embodiments, the fuel is hydrazine. In certain embodiments, the fuel is an ionic liquid fuel. In certain embodiments, the fuel is HGF-A. In certain embodiments, the fuel is HGF-B. In certain embodiments, the poly-nitrated oxetane and fuel are configured for Liquid Propulsion Divert and Attitude Control Systems.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
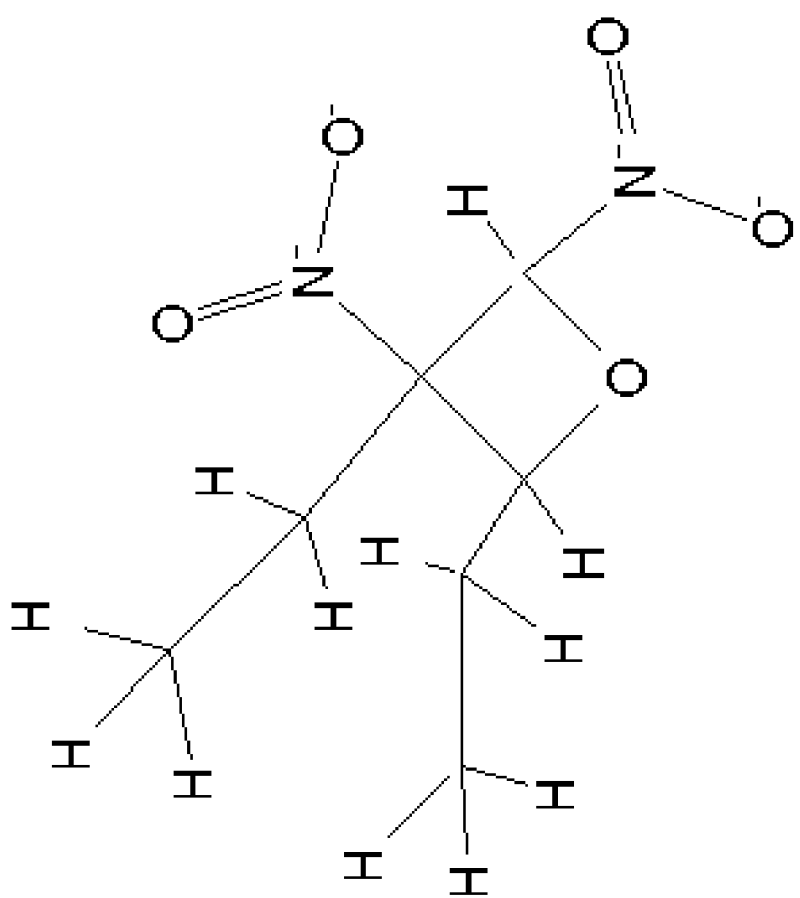
FIG. 1 is an illustration depicting the chemical structure of poly-nitrated oxetane.

The present disclosure generally pertains to green oxidizer compositions and method of synthesizing and using the same. Such green oxidizers are stable, may be used in conventional bipropellant thrusters, including, but not limited to LDACS applications, and offer several benefits over conventional oxidizers with respect to toxicity and/or corrosion. The present disclosure also relates to methods of synthesizing poly-nitrated oxetane, a green oxidizer, in an Argon-rich environment.

As used herein, "HGF" refers to hypergolic green fuel.

As used herein, "NMR" refers to nuclear magnetic resonance.

As used herein, "product" refers to poly-nitrated oxetane or compositions comprising poly-nitrated oxetane, as applicable.

The present disclosure contemplates a method of synthesizing poly-nitrated oxetane comprising the steps of: flushing an empty reactor with Argon so that the entire synthesis process occurs within an Argon environment; adding fuming nitric acid to sulfuric acid (the nitrating mixture); cooling the nitrating mixture to 0° C.; mixing the nitrating mixture with a stir bar; slowly adding a 3-hydroxyoxetane mixture to the nitrating mixture to form a reaction mixture; stopping the stirrer while adding 3-hydroxyoxetane and resuming mixing the reaction mixture in between the additions; stirring the reaction mixture at room temperature for one additional hour at room temperature; quenching the reaction mixture with deionized water with ice; and allowing the resulting poly-nitrated oxetane to settle to the bottom of the reactor and separate from the aqueous layer. The poly-nitrated oxetane may be collected. The moisture content in the resulting poly-nitrated oxetane may be reduced by vacuum evaporation.

The synthesis of poly-nitrated oxetane is mixing-sensitive, which means the reaction is particularly sensitive to the rate at which the reactants are mixed together. The limiting factor in synthesizing poly-nitrated oxetane is the exothermic reaction heat removal; therefore, vigorous heat exchange is needed at the reaction sites to significantly slow down the primary reaction rate thus minimizing any secondary reaction(s). The balance between heat removal and primary reaction rate can be achieved by manipulating the Damkohler number for this reaction.

A necessary condition for a reaction is the collision of two reactant molecules. Two different Damkohler numbers relate the reaction rate to the convective mass transfer (Equation 1 or Type 1) and the reaction rate to the diffusive mass transport as expressed in (Equation 2 or Type 2) as shown below.

First Damkohler number $$Da_1 = \frac{L * k_n * C_A^{n-1}}{U} = \frac{\text{reaction rate}}{\text{convective mass transport rate}} \quad (1)$$

Second Damkohler number $$Da_2 = \frac{L^2 * k_n * C_A^{n-1}}{D} = \frac{\text{reaction rate}}{\text{molecular diffusion mass transport rate}} \quad (2)$$

A large Damkohler number (>1) means the reaction rate is greater than mass transport rate; therefore the reaction is mass transport limited. A small Damkohler number (<1) means mass transport rate is faster than the reaction rate, thus mass transport reaches an equilibrium well before the reaction is at equilibrium. At the same chemical reaction rate, the molecular diffusion rate is usually of magnitude $10^{-5}$, resulting in a large Damkohler number, which means the reaction is limited by diffusive flux. While convective mass transfer rate is of magnitude $10^{-2}$, resulting in a smaller Damkohler number, which means the reaction is limited by the reaction rate. Large Damkohler numbers often lead to a run-away reaction particularly when working with energetic compounds since $k_n$, the reaction rate constant, is a function of temperature. Therefore, small Damkohler numbers under controlled reaction temperatures are most desirable when synthesizing energetic compounds.

As an example, when adding 3-hydroxyoxetane to the reaction, the reaction should be controlled by a diffusion limited mechanism, which is governed by the second Damkohler number. This is achieved without mixing when adding 3-hydroxyoxetane to the nitrating mixture. Since the nitrating mixture is very viscous, without mixing, 3-hydroxyoxetane and the nitrating mixture act as a biphasic system with a very low diffusion rate. Reaction can only occur at localized regions where 3-hydroxyoxetane and the nitrating mixture collide. Due to the low diffusion rate and small doses of 3-hydroxyoxetane added, the heat produced is low and does not result in degradation of the product. It was found that due to high viscosity, vigorous mixing results in high reaction rate and high temperature gradients localized in the region near the feed point. The inadequate dissipation of heat causes degradation to the product that was formed. After 3-hydroxyoxetane has spread across the surface of the nitrating mixture at approximately a monolayer thickness, only then is vigorous mixing initiated. This results in reaction governed by the first Damkohler number, where there is a sufficient amount of mixing to dissipate heat very quickly. The large surface area between 3-hydroxyoxetane and the nitrating mixture also ensures that localized elevated temperatures do not occur. Thus the large scale synthesis of poly-nitrated oxetane requires significant timing between non-mixing and vigorous mixing steps to produce the final stable produce in high yield. The stir bar used in synthesis of poly-nitrated oxetane should be as tall as the reactant volume to maximize yield, because a typical sized stir bar does not provide adequate reactant mixing and heat dissipation, resulting in runaway reactions and loss of product. When this method is used, the reaction is limited by the size and shape of the stirrer. This ratio of stirrer height to reactor volume, and pulsed addition in the non-mixing mode to the vigorous mixing mode, can be scaled-up in commercial reactors.

Gravity separation can eliminate most of the spent acid, but some nitric acid, sulfuric acid, and water mixture may remain leftover in the product. Such residual compounds may cause slow decomposition of the poly-nitrated oxetane product, which results in loss of hypergolicity of such product. The reaction must be quenched by ice water with excess ice and well mixing so the ice must remain present in excess during the entire quenching process. When the reaction mixture, particular leftover acids, comes into contact with water, however, an exothermic reaction occurs. Therefore, it is essential to keep the reaction mixture as close to 0° C. as possible during quench by cooling the reaction immediately with ice, otherwise heat and water will cause the poly-nitrated oxetane to hydrolyze and decompose. If the aqueous temperature and the amount of ice present are not rigorously observed, the quenching mixture may overheat the product. Then the product will hydrolyze and dissolve into water, resulting in one homogenous aqueous layer, no organic layer and loss of product. The moisture content in the poly-nitrated product may be removed using a vacuum evaporator with water temperature at 38° C. for 5-8 hours. However, the higher temperature improves the miscibility of water with poly-nitrated oxetane and decreases the moisture removal efficiency. It was found that the product may be frozen, resulting in a clear top layer that separates from the poly-nitrated oxetane product and which can be simply decanted.

The present disclosure also contemplates a bipropellant composition for use in thrusters. The composition comprises poly-nitrated oxetane and a fuel. The fuel may be hydrazine or an ionic liquid fuel or hypergolic green fuel, such as HGF-A or HGF-B. The composition may also be configured for use in Liquid Propulsion Divert and Attitude Control Systems. A monopropellant composition is also contemplated and may comprise poly-nitrated oxetane, which releases $NO_2$ when heated.

The present disclosure also contemplates a method of propulsion comprising spraying poly-nitrated oxetane and a fuel within a combustion chamber, which may be pre-heated, of a thruster. The fuel may be hydrazine or an ionic liquid fuel or hypergolic green fuel, such as HGF-A or HGF-B. In some embodiments, the propulsion system is configured for LDACS applications.

Experimental Results

Figure 2:
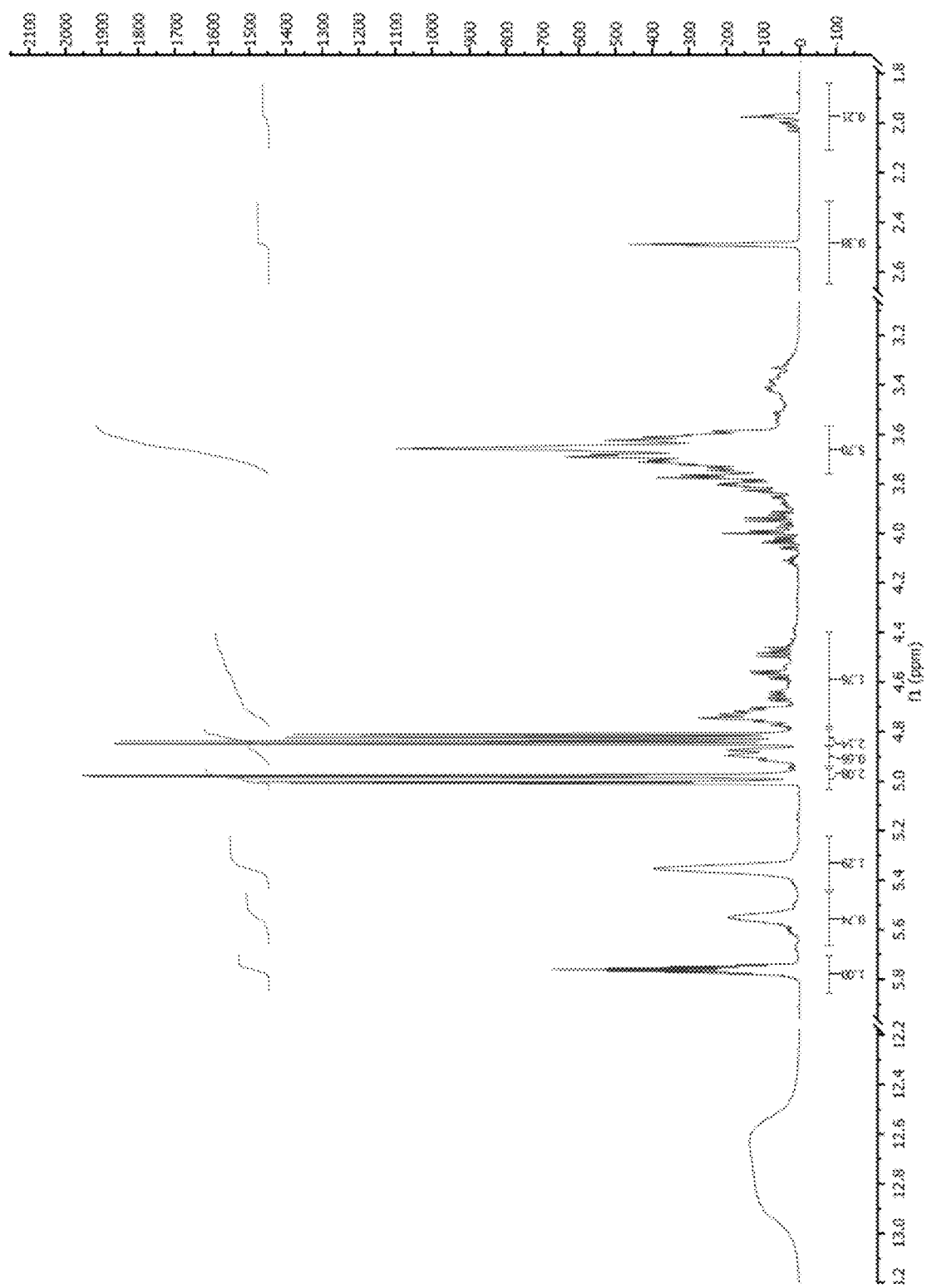
FIG. 2 is a proton NMR spectrum of newly synthesized poly-nitrated oxetane.
Figure 3:
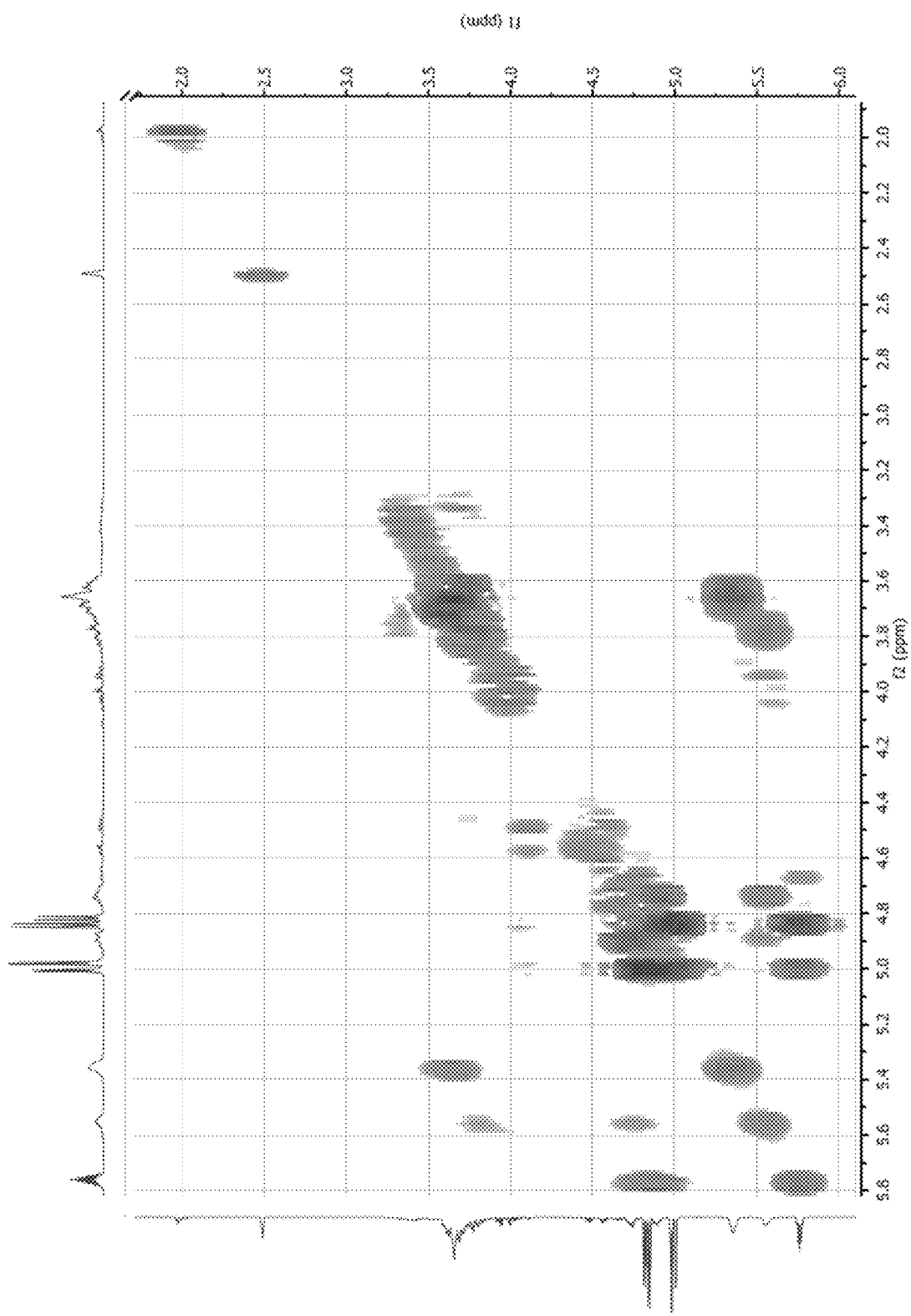
FIG. 3 is a COSY NMR spectrum of newly synthesized poly-nitrated oxetane.
Figure 4:
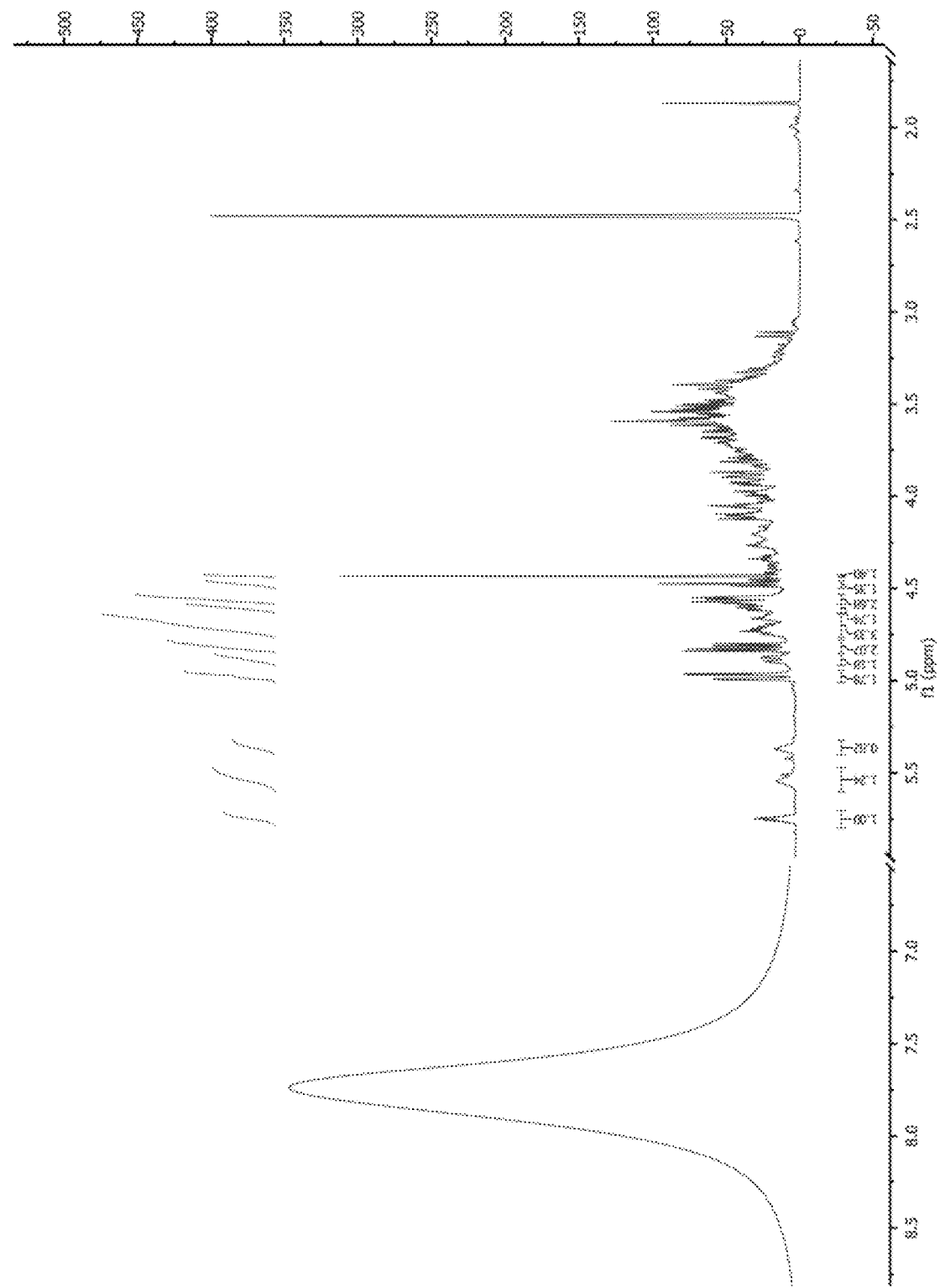
FIG. 4 is a proton NMR spectrum of poly-nitrated oxetane after decomposition in air.
Figure 5:
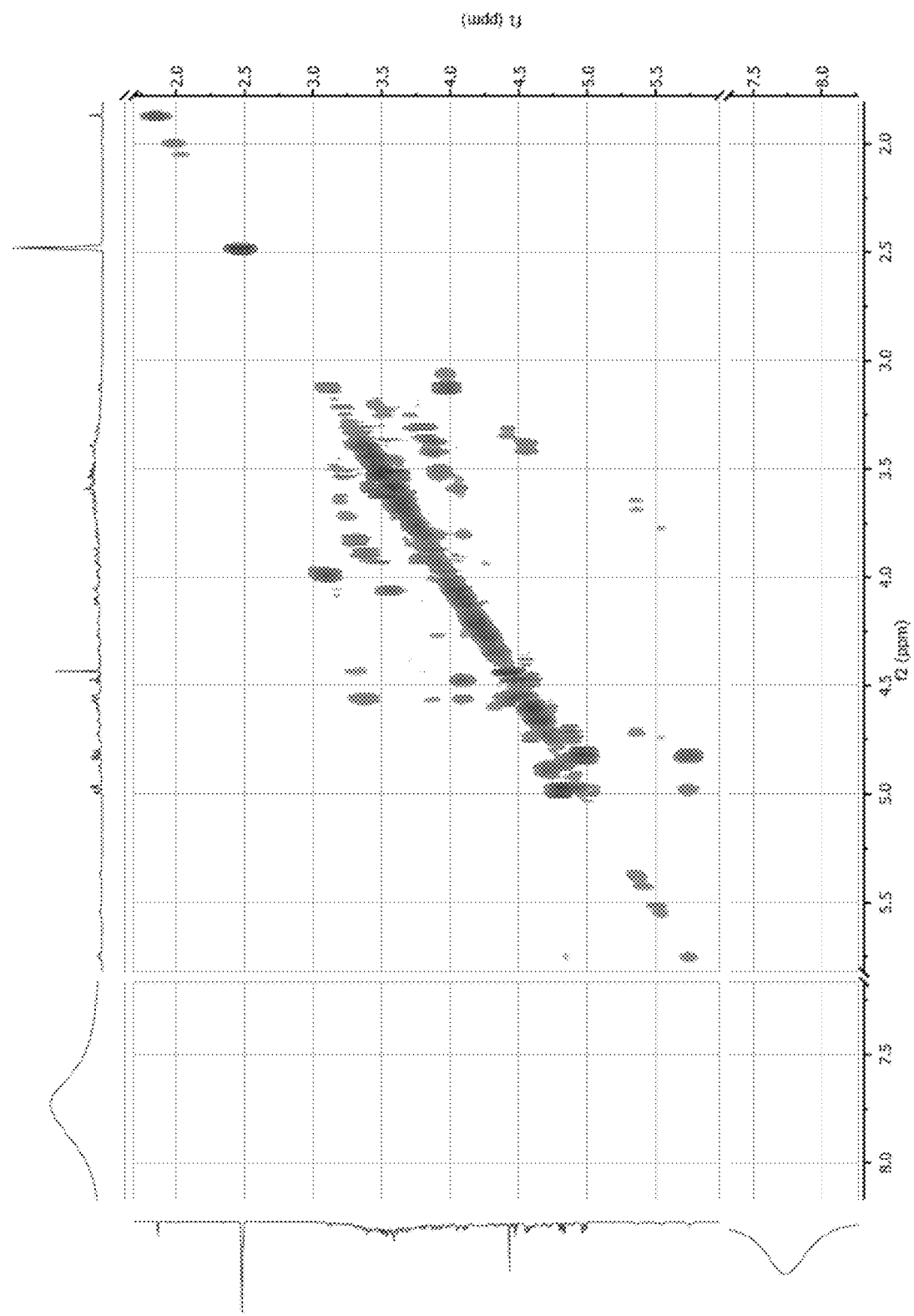
FIG. 5 is a COSY NMR spectrum of poly-nitrated oxetane after decomposition in air.
Figure 6:
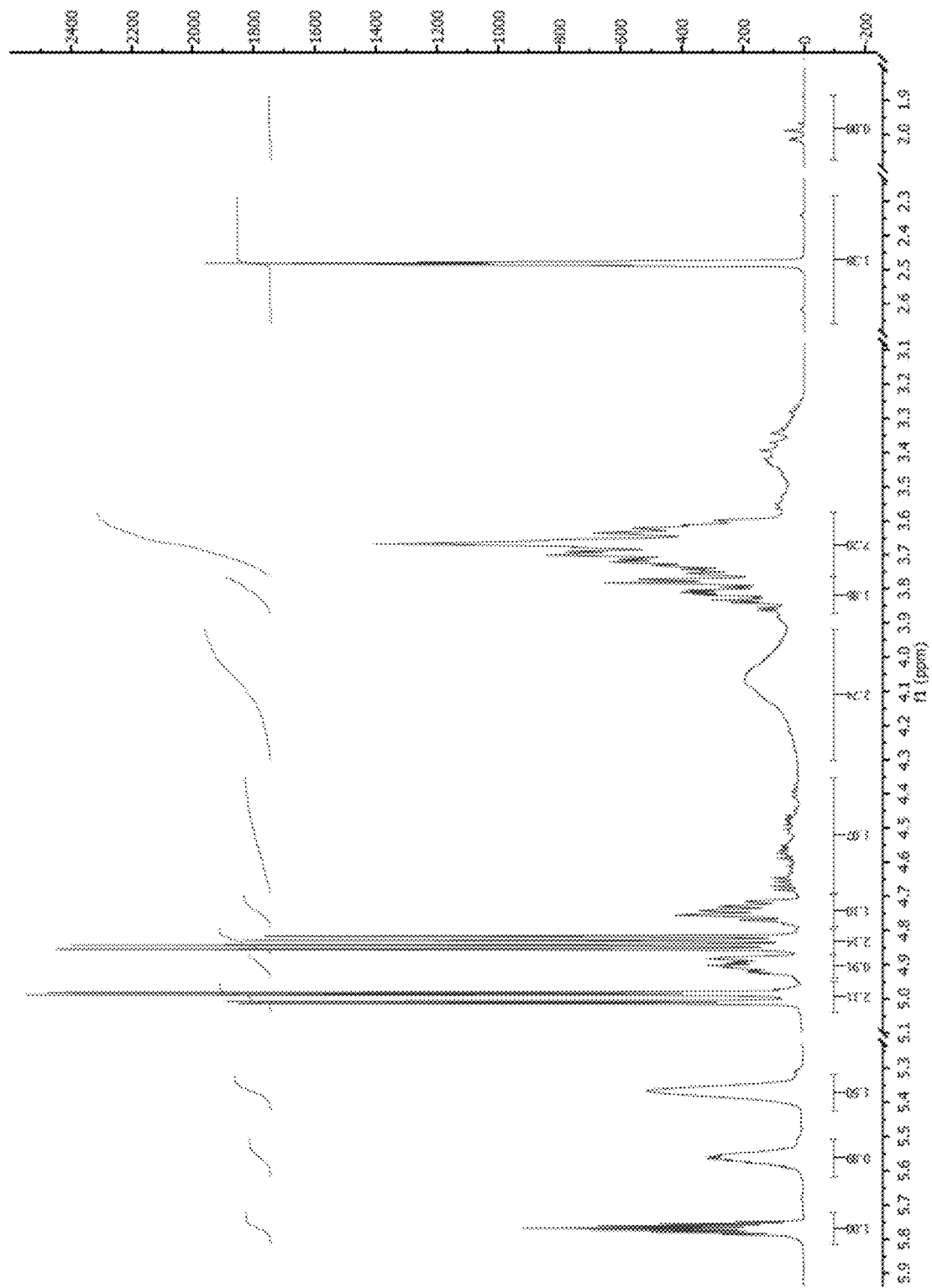
FIG. 6 is a proton NMR spectrum of ice solution back extracted poly-nitrated oxetane.
Figure 7:
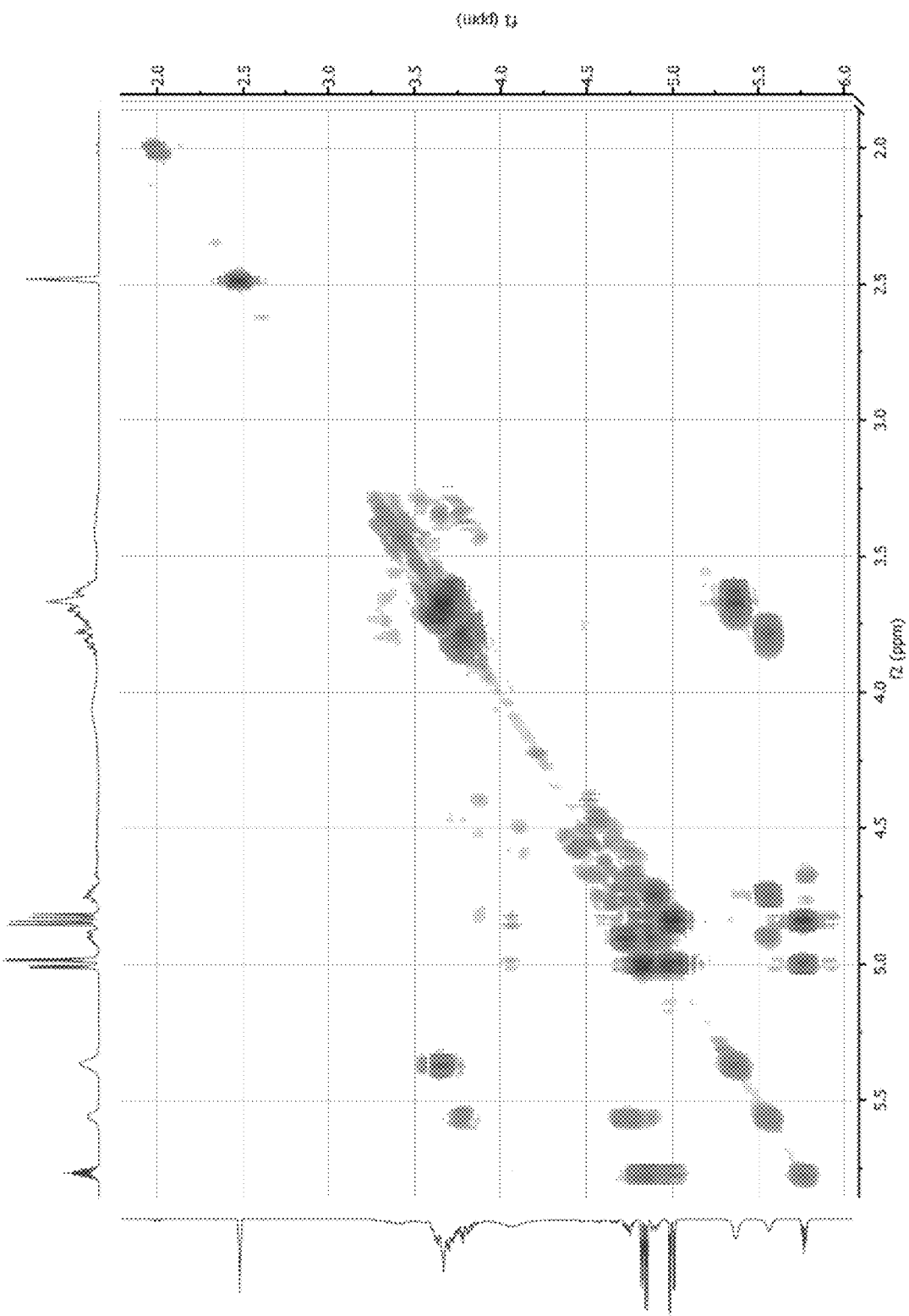
FIG. 7 is a COSY NMR spectrum of ice solution back extracted poly-nitrated oxetane.

Proton NMR was used by the applicants to determine the structure of poly-nitrated oxetane shown in FIG. 1. The proton NMR of poly-nitrated oxetane prepared in a small batch is shown in FIG. 2. Peaks at 12.7 ppm are the nitronium ion/nitric acid complex and water peak. The increase in intensity of the peak at 12.7 ppm when comparing FIG. 3 to FIG. 2 is possibly due to the reactive unstable nitronium ion attacking poly-nitrated oxetane resulting in an increase in water content. The decomposition of the poly-nitrated oxetane can be directly observed as the compound slowly gives off a red fume (nitrogen dioxide) after being exposed to air. When comparing the COSY NMR spectra before (FIG. 4) and after (FIG. 5) decomposition, it clearly shows that the proton spin coupling has changed significantly. FIG. 6 clearly shows that after poly-nitrated oxetane was extracted by the ice slurry method and dried by rotary evaporation, there was no nitronium ion/nitric acid complex and no water peak at 12.7 ppm. FIG. 7, however, shows the proton peaks of proton NMR between 4.2 and 3.8 ppm were displaced, which means water back extraction might have a hydrolysis effect on the structure of the oxetane ring stabilizing the final product.

NMR diagrams were also used to deduce the structure of poly-nitrated oxetane (FIG. 1) prepared with excess ice, based on 500 MHz NMR as discussed herein. Other green oxidizer variants, however, substituted on the oxetane backbone may exist when prepared under controlled reaction conditions, back extracted with deionized water with an excess of ice.

Figure 8:
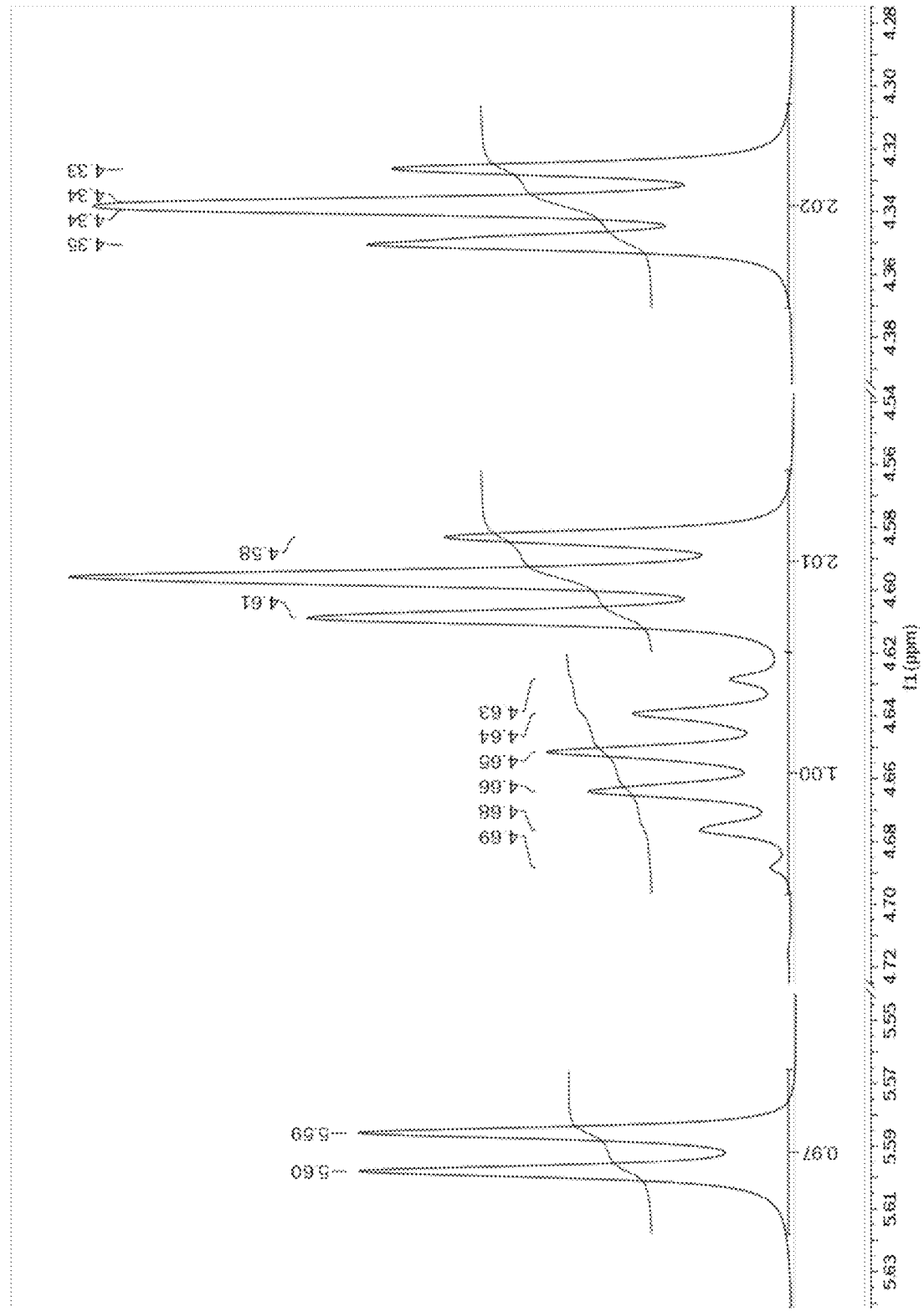
FIG. 8 is a proton NMR spectra of 3-hydroxyoxetane.
Figure 9:
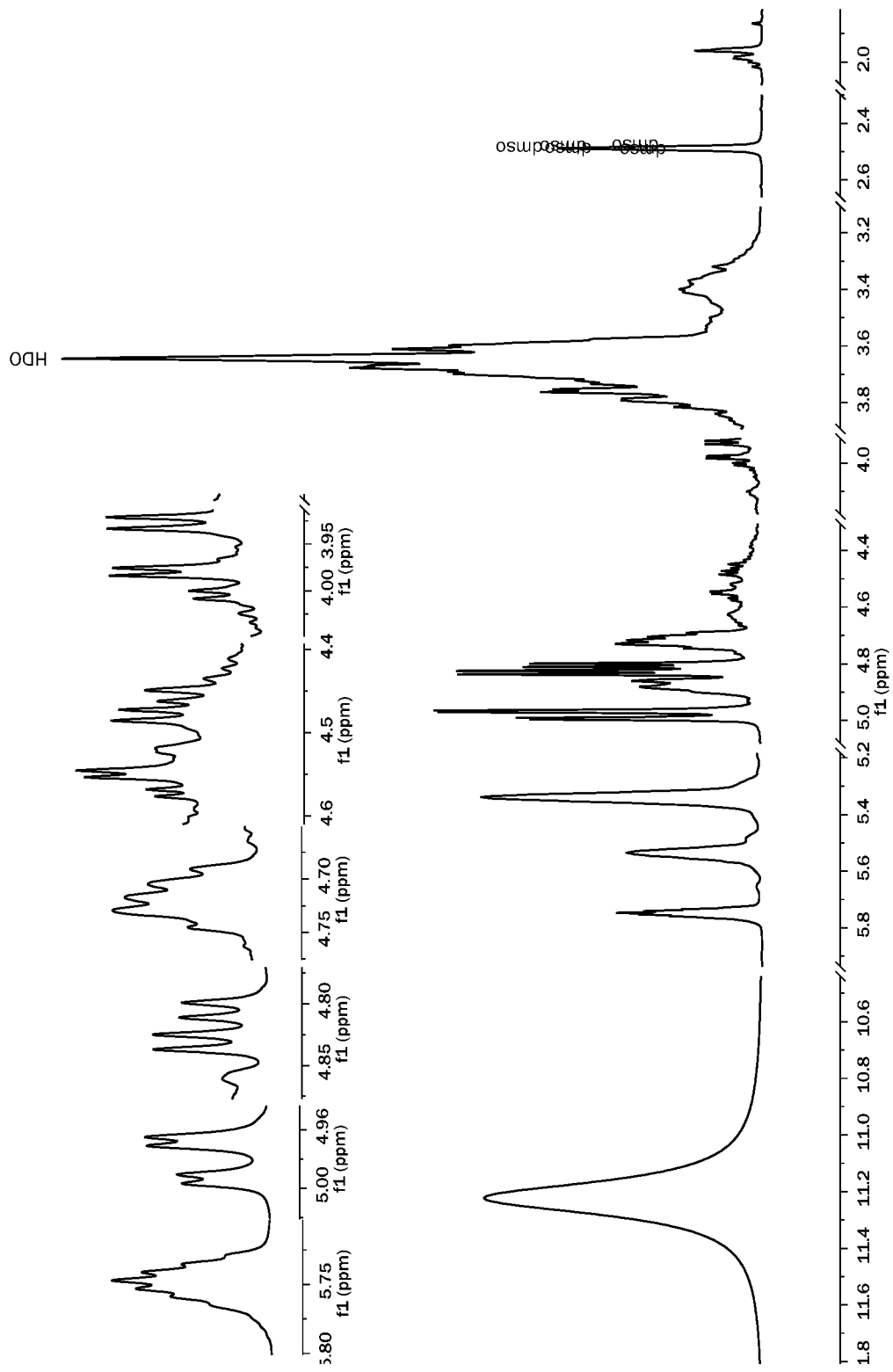
FIG. 9 is a proton NMR spectra of poly-nitrated oxetane.
Figure 18:
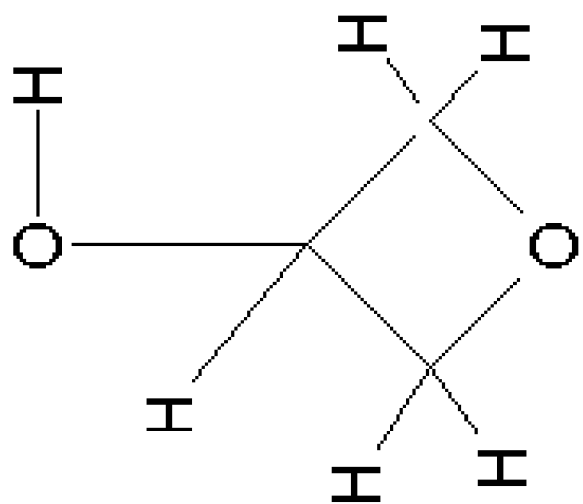
FIG. 18 is an illustration depicting the chemical structure of [VII].

Applicants performed experiments on the starting material, 3-hydroxyoxetane, and the product, poly-nitrated oxetane, in solvent deuterated dimethyl sulfoxide (DMSO). FIG. 8 and FIG. 9 show the proton NMR spectra of 3-hydroxyoxetane and poly-nitrated oxetane. The proton peaks at 4.6 ppm and 4.3 ppm on FIG. 8, corresponding to H2 and H3 on FIG. 18, are two doublet of doublet that overlays into two peaks that have the appearance of triplets.

Figure 10:
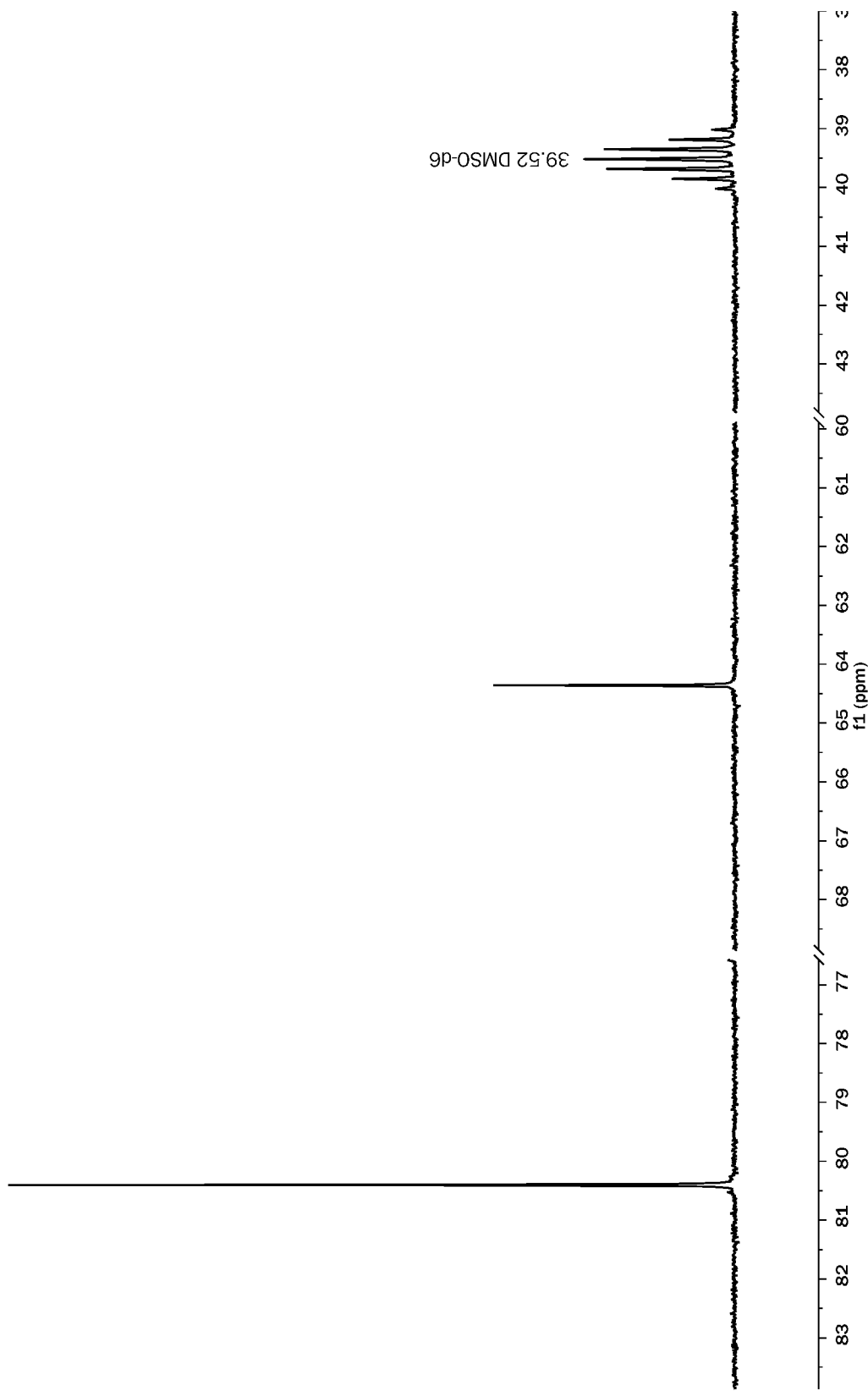
FIG. 10 is a carbon NMR spectra of 3-hydroxyoxetane.
Figure 11:
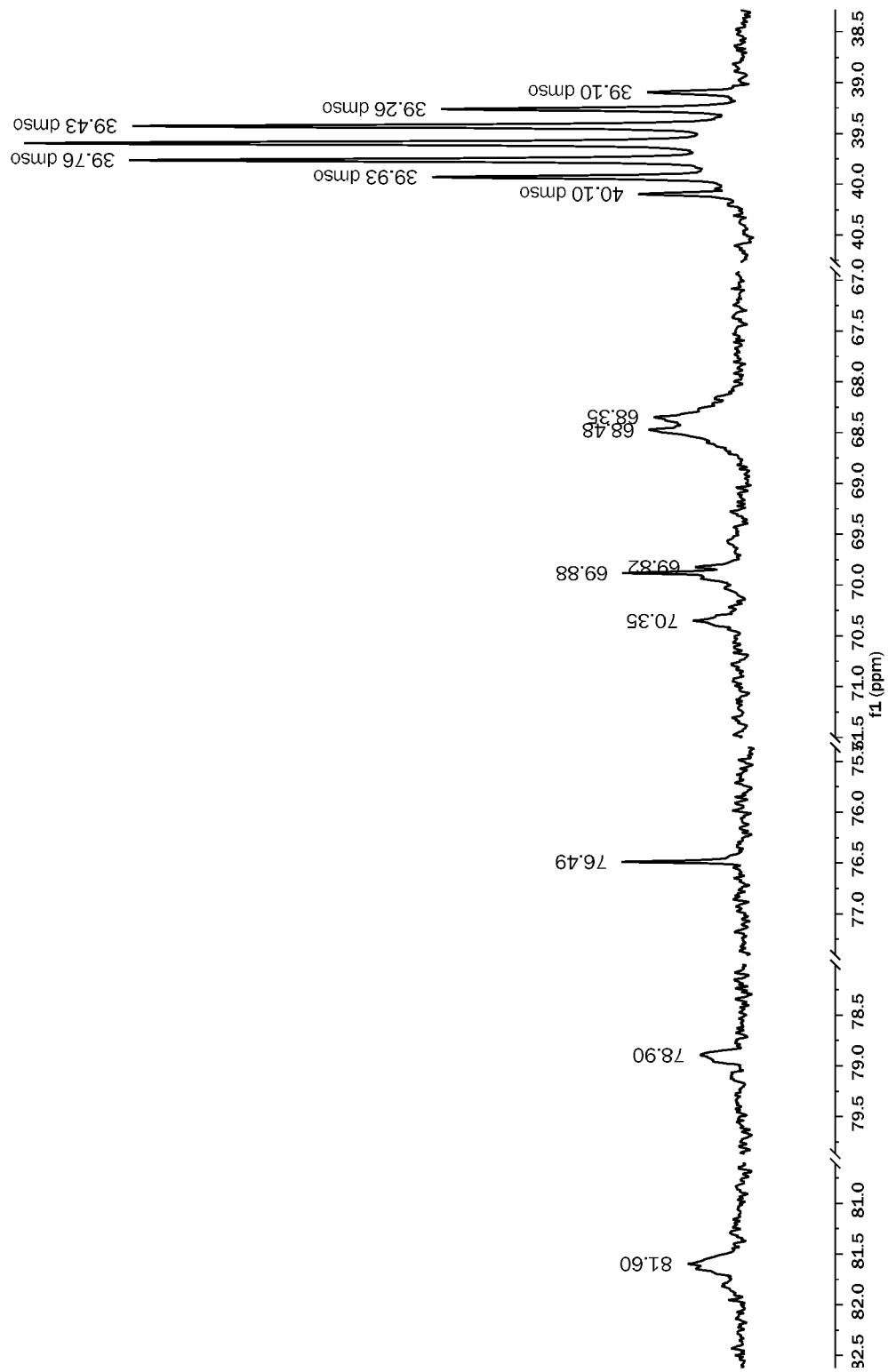
FIG. 11 is a carbon NMR spectra of poly-nitrated oxetane.
Figure 12:
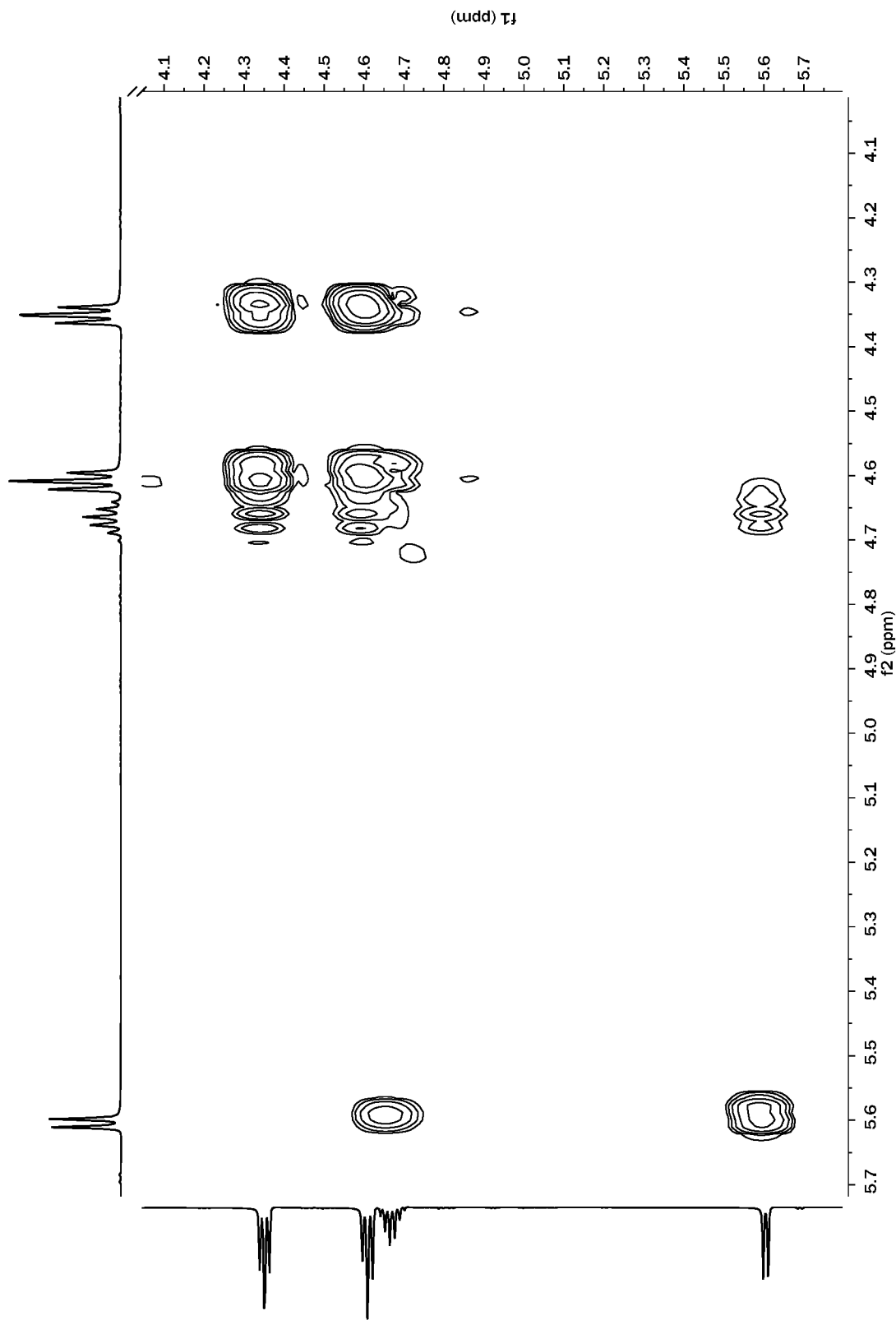
FIG. 12 is a correlation spectroscopy (COSY) NMR spectra of 3-hydroxyoxetane.
Figure 14:
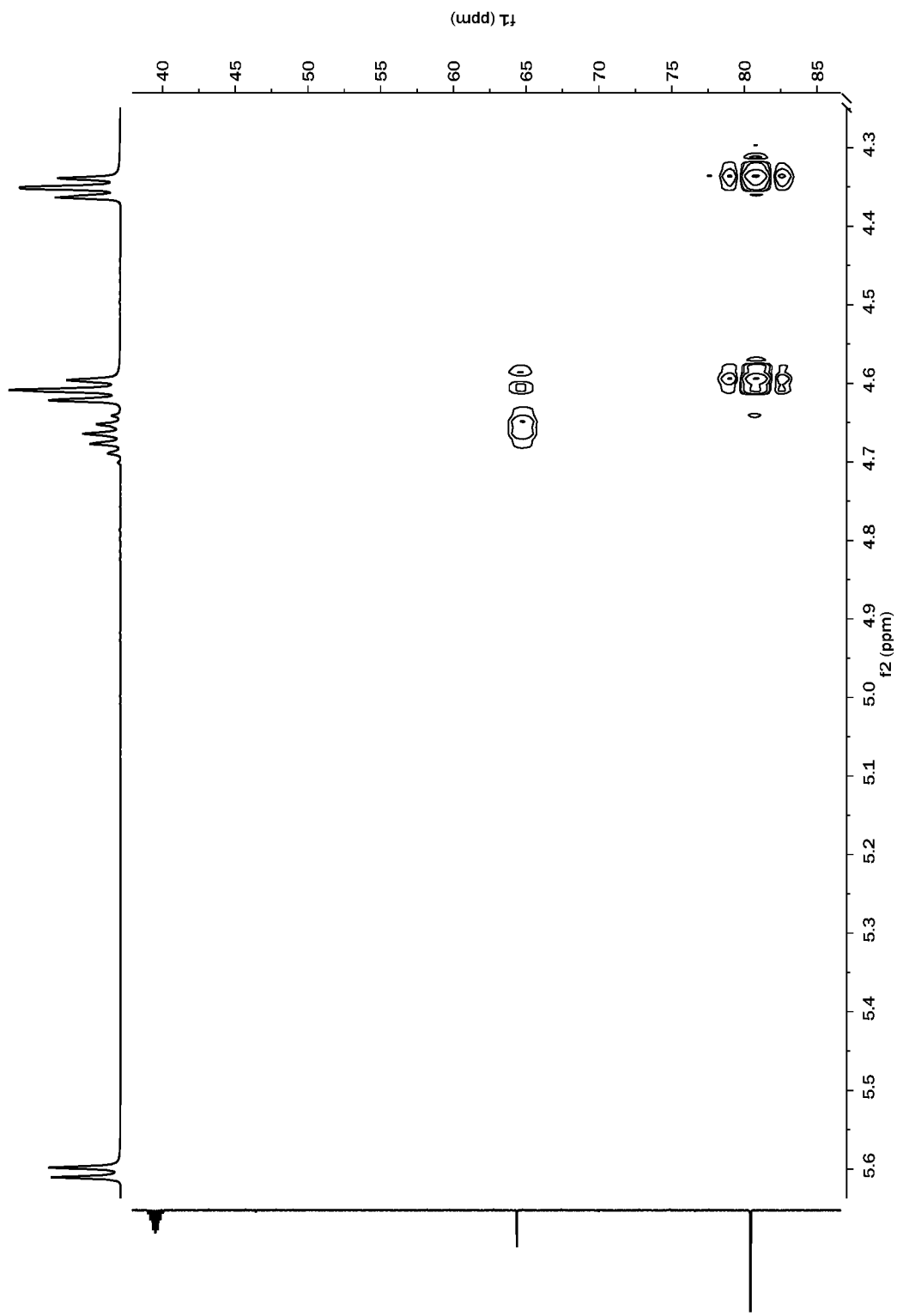
FIG. 14 is a heteronuclear single quantum coherence spectroscopy (HSQC) NMR spectra of 3-hydroxyoxetane.

FIG. 10 shows that 3-hydroxyoxetane has two carbon peaks while FIG. 11 shows that there are seven carbon peaks present in the poly-nitrated oxetane product. It can be derived from FIG. 12 and FIG. 14 that the proton peak at 5.6 ppm is the H1 hydrogen from FIG. 18 while the 4.65 ppm peak is the H4 hydrogen from FIG. 18.

Figure 13:
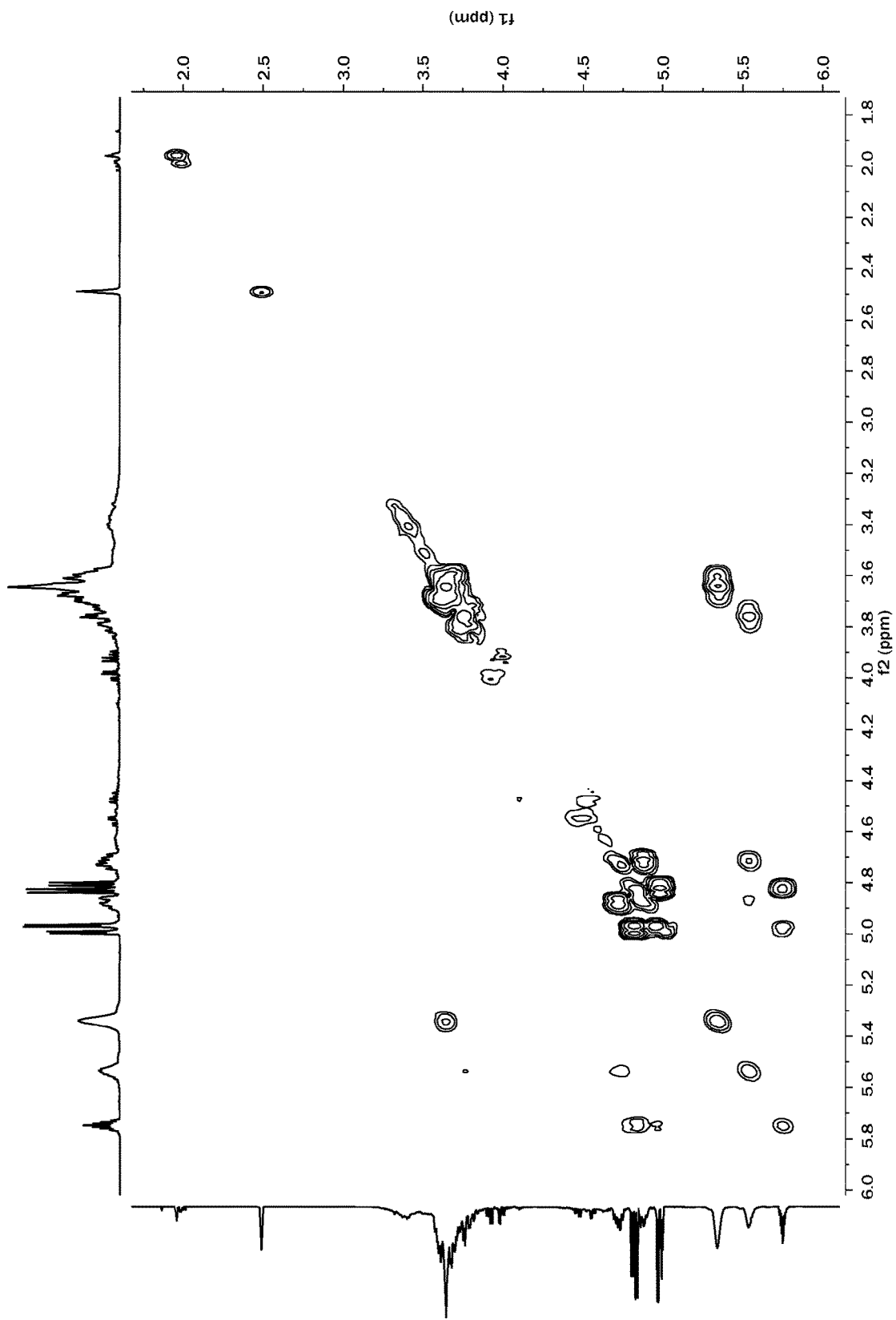
FIG. 13 is a correlation spectroscopy (COSY) NMR spectra of poly-nitrated oxetane.
Figure 15:
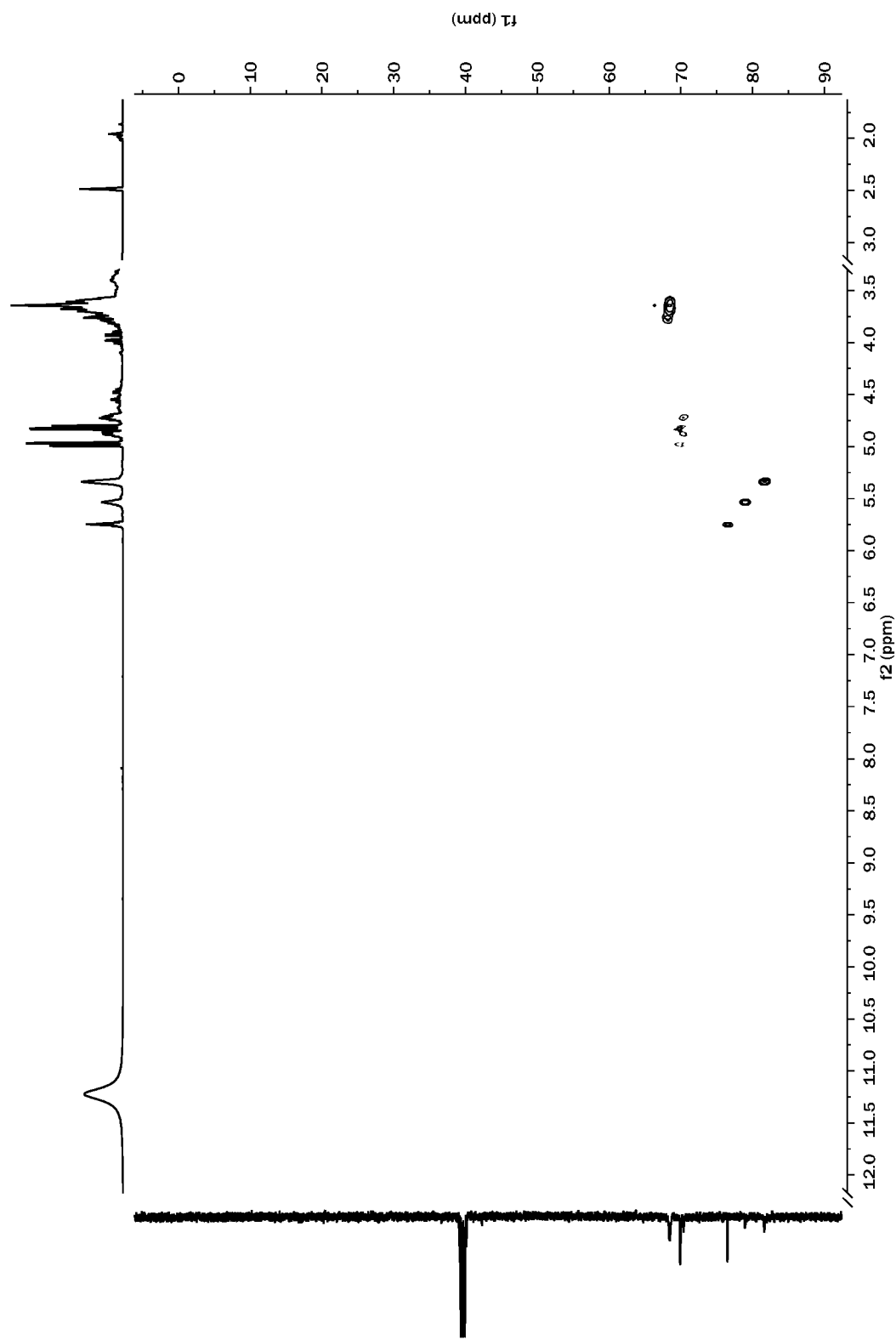
FIG. 15 is a heteronuclear single quantum coherence spectroscopy (HSQC) NMR spectra of poly-nitrated oxetane.
Figure 16:
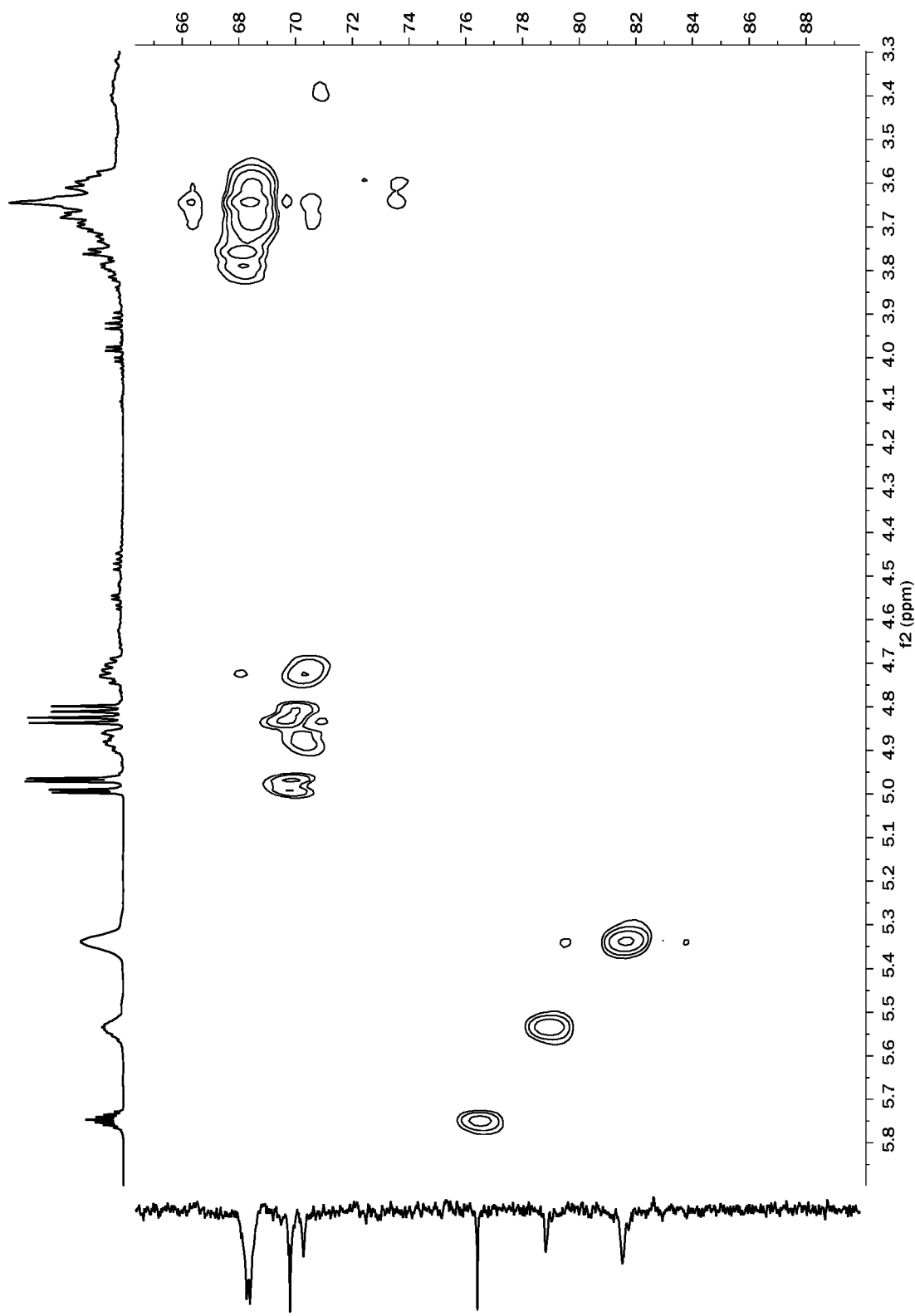
FIG. 16 is a zoomed view of HSQC NMR spectra of poly-nitrated oxetane.
Figure 17:
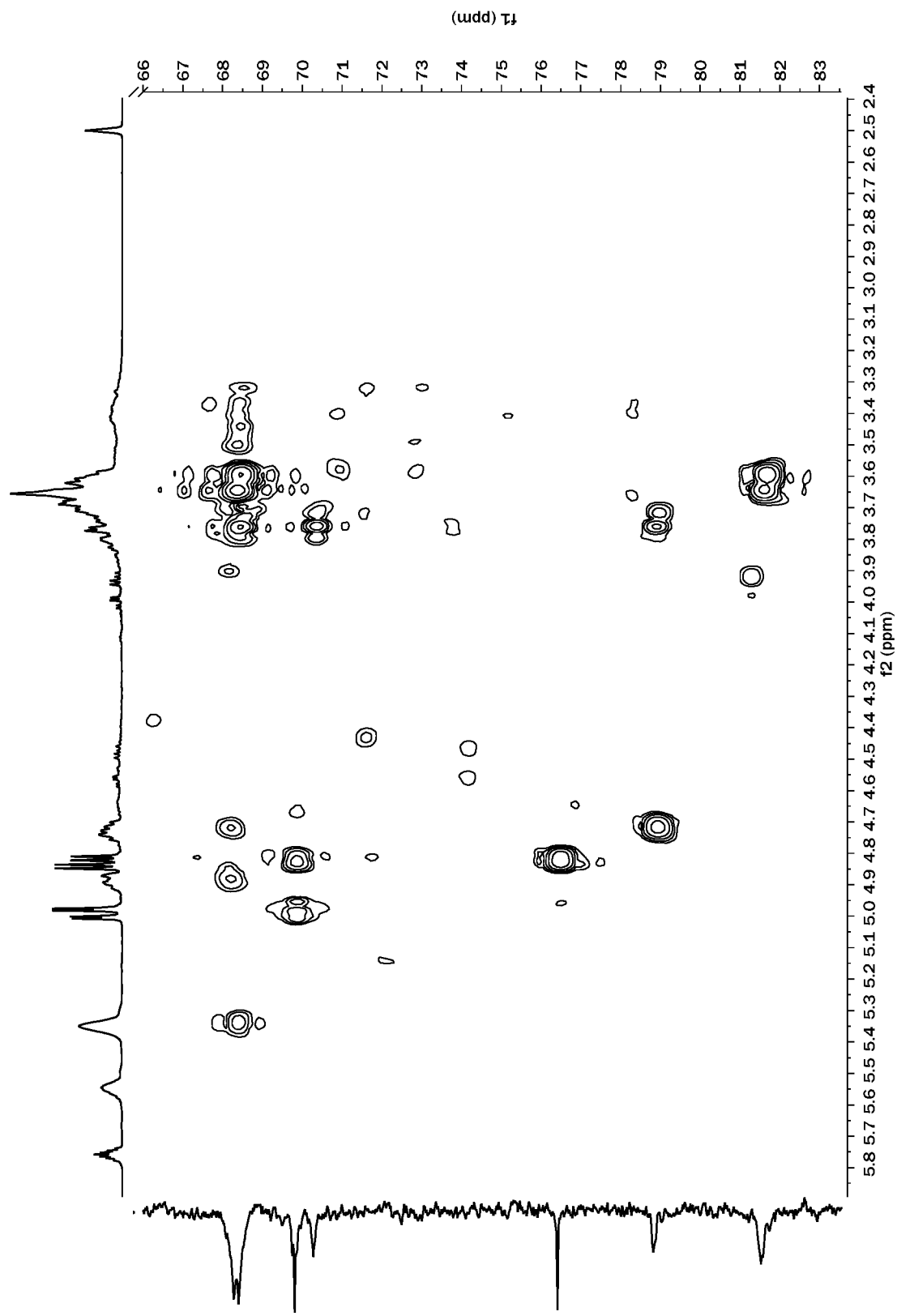
FIG. 17 is a heteronuclear Multiple Bond Correlation (HMBC) NMR spectra of poly-nitrated oxetane.

FIG. 9 clearly shows that that are sulfuric acid and water impurities in the product which resulted in peaks at 11.2 ppm and 3.6 ppm, where the OH peak on sulfuric acid and the OH of water resulted in strong peaks, respectively. It can be inferred from FIG. 13, FIG. 14, and FIG. 15 that the conversion rate of 3-hydroxyoxetane to poly-nitrated oxetane was approximately 30-50%, because peaks at 4.975 ppm and 4.825 ppm clearly show that doublet of doubles peaks present in the NMR of 3-hydroxyoxetane, while multiplicity peak at 5.77 ppm is the peak resulting from H4 on FIG. 18. From FIG. 13, FIG. 16, and FIG. 17, it can be inferred that there are two proton peaks at 70 ppm and 76 ppm, and 3 proton peaks at 5.75 ppm, 4.975 ppm, and 4.825 ppm that only interact with each other but not with any other peaks. These peaks correlates to the NMR spectra of 3-hydroxyoxetane. Therefore, not all 3-hydroxyoxetane was converted to poly-nitrated oxetane when the ratio of sulfuric acid was increased in the nitration mixture. The structure was estimated and shown in FIG. 1. From FIG. 9, the proton integration shows that peaks at 4.9 ppm and 4.7 ppm are single protons in H2 and H3 on FIG. 1. While the H4 that was originally on CII has been dissociated and replaced by an $NO_2$ group. The right hand H3 on FIG. 18 has also dissociated and been replaced by an $NO_2$ group. The left hand H3 on FIG. 18 dissociated, but was replaced by instead a short carbon chain. The carbon chains on CI and CII are from the chain opening reaction that resulted from using short and wide reactors. While the short and wide reactor improved mixing, it can also cause more rapid decomposition of the oxetane ring than other synthesis procedures. The decomposed ring debris attached itself to some of the positions on the oxetane, since the rate of nitration is the slower step.

Applicants back extracted HGF-A and poly-nitrated oxetane with ice, mixed the HGF-A and poly-nitrated oxetane at room temperature, and then injected the HGF-A and poly-nitrated oxetane into a pre-heated reactor such that a hypergolic reaction occurred at 339° F. HGF-B reacted hypergolically with poly-nitrated oxetane back extracted with ice at temperatures as low as 295° F. when premixed with an O/F ratio of 2. The difference between HGF-A and HGF-B depended on the age of the reactants with HGF-B being made from a fresh batch of HEN. These results represent a hypergolic reaction occurring with a green fuel and green oxidizer system. In essence, poly-nitrated oxetane can function as both a monopropellant and, when added to a fuel, perform as a bipropellant. Poly-nitrated oxetane is an $NO_2$ gas generator when heated to specific temperatures with or without a catalyst.

The $NO_2$ gas generation can also be used with the introduction of hypergolic fuels such as AH, MMH, UDMH, Aerozine 50/50 and HGF. An important result was the introduction of MMH into a preheated reactor. Table 1 shows the chemical delay time measured when decomposing poly-nitrated oxetane was reacted with MMH. The CDT was measured as 0.428+/−0.216 msec. This large deviation is tied to inconsistency between timing of the two injections.

Based on the standard deviation for the poly-nitrated oxetane reaction with MMH, the range is 0.212 to 0.644 msec. MMH/RFNA has a measured CDT of 0.220 msec. At higher temperatures, the fuel could not be added to the combustor fast enough and a flame occurred before the fuel dropped out of the injection needle. This timing problem can be addressed using a hypergolic engine with varying valve timing. Further, a heated Platinum or Platinum/Rhodium wire mesh can be used to decompose poly-nitrated oxetane in a manner similar to decomposition of AH, used in monopropellant combustion, using a mesh supported Shell 405 catalyst.

TABLE 1

Results of bipropellant reaction at 252° F. with MMH fuel and O/F of 2

| T (° F.) | CDT (ms) | Standard Deviation (ms) |
|---|---|---|
| 252 | 0.428 | 0.216 |

No reaction occurred when HGF-A was mixed with poly-nitrated oxetane at room temperature. An ignition occurred with the HGF-A/GOX mixture of 339° F. and an O/F ratio of 2. The temperature required was significantly higher than the temperature at which poly-nitrated oxetane reacts as a monopropellant, which is an excellent result for ship-born applications, which require the highest decomposition possible. When the mixture was added to a Platinum or Platinum/Rhodium wire mesh, the hypergolic reaction still occurred, but a lower reactor temperature was not obtained. HGF-A prepared with a slight excess of nitric acid increased thermal stability by 87° F., which may be important for ship-born applications. Long term stability when mixed with poly-nitrated oxetane would simplify rocket motor construction to a single tank, timing valve and preheated Platinum or Platinum/Rhodium mesh, similar to an AH monopropellant thruster design currently in use.

HGF-B reacted hypergolically with poly-nitrated oxetane at temperatures as low as 295° F. when premixed with an O/F ratio of 2. The fuel and oxidizer underwent a reaction when mixed at room temperature. HGF-B increased the ignition temperature from the pure poly-nitrated oxetane at 252° F. to 295° F., an increase of 43° F.

Thus, an oxidized version of HGF termed HGF-A may be suitable as a green bipropellant. The bipropellant reactions disclosed above represent the first time both a green fuel (HGF) and green oxidizer (poly-nitrated oxetane) were successfully tested and may open the door to other green fuels under development once $N_2O_4$, MON, or $MON_3$ are replaced by versions of poly-nitrated oxetane.

To maximize stability, the poly-nitrated oxetane should be stored in a closed container under an inert atmosphere. To test the stability of poly-nitrated oxetane, it was stored in a closed container at room temperature and opened regularly, exposing it to air over the course of one month. The results are shown in Table 2.

TABLE 2

| Time Elapsed (weeks) | Minimum Monopropellant Reaction Temperature (° F.) |
|---|---|
| 0 | 250 |
| 1 | 250 |
| 2 | 250 |
| 3 | 250 |
| 4 | 313 |

To test stability, poly-nitrated oxetane was subjected to UN Test Series 3 Test 3(a)(i) (Bureau of Explosive Impact Sensitivity Test) and UN Test Series 3 Test 3(b)(i) (BAM Friction Sensitivity Test), both of which it passed. Under Test 3(a)(i), the poly-nitrated oxetane was not sensitive to drop impact when tested ten times at drop height of 25 cm using 8-lbs drop weight. Under Test 3(b)(i), the poly-nitrated oxetane was sensitive to a friction load of 240 N, but was not sensitive to a friction load of 160 N, when tested 6 times using BAM Friction Sensitivity apparatus. The result of passing each test is that the poly-nitrated oxetane is considered suitable for transport in the form in which it was tested.

The green oxidizer compositions disclosed herein provide significant benefits compared with conventional oxidizers. Conventional oxidizers are toxic and/or corrosive. The presently disclosed green oxidizer poly-nitrated oxetane, in contrast, reduce or eliminate toxicity and corrosion and are stable (as demonstrated by UN Series 3 Test 3(a)(i) and 3(b)(i) testing). Further, such green oxidizer may be used in conventional bi-propellant thruster technology with minimal modifications. In addition, the green oxidizer described herein may be used as a monopropellant; poly-nitrated oxetane is a liquid at room temperature, but it releases $NO_2$ gas when heated, which may also be used as a monopropellant.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The methodologies and the various embodiments thereof described herein are exemplary. Various other embodiments of the methodologies described herein are possible.

Now, therefore, the following is claimed:

1. A method comprising spraying poly-nitrated oxetane and a fuel within a combustion chamber of a thruster, thereby causing the thruster to generate propulsion.

2. The method of claim 1, wherein the combustion chamber is heated prior to the spraying the poly-nitrated oxetane and the fuel.

3. The method of claim 1, wherein the fuel is hydrazine.

4. The method of claim 1, wherein the fuel is an ionic liquid fuel.

5. The method of claim 4, wherein the fuel is HGF-A.

6. The method of claim 4, wherein the fuel is HGF-B.

* * * * *